United States Patent [19]
Bucala et al.

[11] Patent Number: 5,854,000
[45] Date of Patent: *Dec. 29, 1998

[54] METHODS FOR MEASUREMENT PREDICATED ON THE PRESENCE OF ADVANCED GLYCOSYLATION ENDPRODUCTS IN TOBACCO AND ITS COMBUSTION BYPRODUCTS

[75] Inventors: Richard J. Bucala, Cos Cob, Conn.; Helen Vlassara, Shelter Island; Anthony Cerami, New York, both of N.Y.; Henry W. Founds, Mendham, N.J.

[73] Assignees: Alteon Inc., Ramsey, N.J.; The Picower Institute For Medical Research, Manhasset, N.Y.

[*] Notice: This patent issued on a continued prosecution application filed under 37 CFR 1.53(d), and is subject to the twenty year patent term provisions of 35 U.S.C. 154(a)(2).

[21] Appl. No.: 617,349

[22] Filed: Mar. 18, 1996

Related U.S. Application Data

[63] Continuation-in-part of Ser. No. 613,234, Mar. 8, 1996.

[60] Provisional application No. 60/009,219, Dec. 26, 1995.

[51] Int. Cl.⁶ .................. G01N 33/53; G01N 33/542; G01N 33/537; G01N 33/543; G01N 30/02; G01N 30/90; G01N 33/566; G01N 33/551

[52] U.S. Cl. .................. 435/7.1; 436/518; 436/524; 436/525; 436/526; 436/527; 436/528; 436/529; 436/530; 436/531; 436/803; 436/501; 436/547; 436/815; 436/900; 436/901; 435/414; 435/4; 435/7.1; 435/7.9; 435/7.91; 435/7.92; 435/7.93; 435/7.94; 435/7.95; 435/325; 435/345; 530/387.1; 530/389.9; 530/389.8; 73/19.02

[58] Field of Search .................. 436/518, 524–531, 436/501, 547, 815, 900, 901, 803; 530/387.1, 388.9, 389.8; 435/4, 7.1, 7.9–7.95, 240.26, 414, 325, 345; 73/19.02

[56] References Cited

U.S. PATENT DOCUMENTS

| | | | |
|---|---|---|---|
| 4,665,192 | 5/1987 | Cerami | 548/336 |
| 5,017,696 | 5/1991 | Farmar et al. | 536/18.7 |

OTHER PUBLICATIONS

Chen et al. (1992) *J. Aerosol Med.* 5:19–30.

Chen et al. (1989) *Inhalation Toxicol.* 1:331–47.

Hayase et al., "Aging of Proteins: Immunological Detection of a Glucose–derived Pyrrole Formed during Maillard Reaction in vivo", *J. Biol. Chem.*, 263:3758–3764 (1989).

Sell, D. and Monnier V. "Structure Elucidation of a Senescence Cross–link from Human Extracellular Matrix", *J. Biol. Chem.*, 264:21597–21602 (1989).

*Primary Examiner*—Sheela Huff
*Attorney, Agent, or Firm*—Klauber & Jackson

[57] ABSTRACT

Methods are disclosed for measuring the accumulation of advanced glycosylation endproducts (AGEs), which are predicated on the discovery that such AGEs are present in tobacco and its byproducts. More particularly, the methods focus on the observation that individuals who smoke or otherwise use tobacco have increased levels of AGEs over non-smoking individuals. The present methods relate to the measurement of AGE levels in both individuals and in tobacco and its byproduct, smoke. Methods are also disclosed for the evaluation of the tobacco products to determine their storage status and organoleptic capacity and potential, as well as for the treatment of the ambient to lower AGE levels. For example, air or other samples may be taken and evaluated by a dosimeter or like device, to determine whether AGE levels exceed normal, after which measures could be implemented to remediate the ambient condition. All such methods and corresponding materials are contemplated and included.

11 Claims, 4 Drawing Sheets

FIG. 4

METHODS FOR MEASUREMENT PREDICATED ON THE PRESENCE OF ADVANCED GLYCOSYLATION ENDPRODUCTS IN TOBACCO AND ITS COMBUSTION BYPRODUCTS

CROSS REFERENCE TO RELATED APPLICATIONS

The present application is a Continuation-In-Part of application Ser. No. 08/613,234 filed on Mar. 8, 1996, now abandoned by the inventors herein. This application claims priority from U.S. Provisional Application Ser. No. 60/009,219, filed Dec. 26, 1995.

TECHNICAL FIELD OF THE INVENTION

The present invention relates generally to the correlation between the use of tobacco products such as cigarettes, and the presence of advanced glycosylation endproducts (AGEs), and to the diagnostic applications to which this observation and relationship may be beneficially directed. More particularly, the invention directs itself to the observation that the consumption of tobacco products increases the amount of AGEs in vivo, with concomitant increases in the risk and incidence of maladies associated with both smoking and AGE accumulation and to the detection of AGEs in tobacco, tobacco smoke and extracts thereof, as well as in tobacco users, both to detect undesirable excesses in AGE levels and to evaluate tobacco and smoking materials on a commercial scale.

BACKGROUND OF THE INVENTION

The deleterious effects of tobacco smoking on human health have been extensively documented. Among other things, such conditions as cancer and coronary heart disease are dramatically elevated in incidence and severity in the case of smokers, and such patients likewise present significant alterations in lipoprotein profiles and increases in oxidized LDLs. Increased occurrence and severity of coronary heart disease and dyslipidemia, among other things, have also been observed in patients having elevated levels of advanced glycosylation endproducts (AGEs), and the coincidence of these observations set the stage for the discovery that underlies the present invention.

The nonenzymatic reactions between glucose and proteins has been recognized for many years, but molecular details of these reactions, and the biological and medical consequences of nonenzymatic glycation in vivo, are still emerging today. The earliest recognized manifestation of nonenzymatic glycation was in the appearance of brown pigments during the cooking of food, which was identified by Maillard in 1912, and lent the term "browning" to this branch of food chemistry. Maillard observed that glucose or other reducing sugars react spontaneously with amino-containing compounds such as amino acids and peptides to form initial Schiff base adducts. This condensation product then undergoes a series of additional spontaneous dehydrations, rearrangements and other reactions to form the class of brown pigments, now known as advanced glycosylation endproducts, or AGEs.

In the years that followed its initial discovery, food chemists studied the Maillard reaction in detail and determined that stored and heat-treated foods undergo nonenzymatic browning as a development of the initial reaction between glucose and the polypeptide chain, and that the proteins are resultingly crosslinked and correspondingly exhibit decreased bioavailability. At this point, it was determined that the pigments responsible for the development of the brown color in protein glycosylation (or advanced glycation) also possess characteristic absorptive spectra and fluorescent properties.

The reaction between reducing sugars and food constituents discussed above was found in recent years to have its parallel in vivo. Thus, the nonenzymatic rearrangement of the initial Schiff base formed by addition of glucose to a free amino group on a protein forms the stable amino, 1-deoxy ketosyl adduct known as the Amadori product. (A parallel reaction involving a reducing ketose rather than an aldose generates an early glycation product known as the Heyns rearrangement product). Accumulation of this early glycation adduct has been shown to occur with hemoglobin, wherein a rearrangement of the amino terminus of the β-chain of hemoglobin following an initial reaction with glucose forms the modified hemoglobin known as hemoglobin $A_{1c}$, a clinically important marker of glucose control in diabetes. Glycation reactions have also been found to occur with a variety of other body proteins, such as lens crystallins, collagen nerve proteins, and low density lipoproteins, as well as DNA and aminophospholipids.

The Maillard browning process generates a widely diverse array of advanced glycosylation products, each of which occurs in very low yield. This diversity has made identification and structural determination of specific AGEs a difficult proposition. In U.S. Pat. No. 4,665,192 the fluorescent chromophore 2-(2-furoyl)-4(5)-2(furanyl)-1H-imidazole was isolated and identified from certain browned polypeptides such as bovine serum albumin and poly-L-lysine. This success encouraged the subsequent identification of additional advanced glycosylation endproducts and assisted additional investigations seeking to clarify the chemistry of the protein aging process and to identify the specific reactants, intermediates and products involved in order to develop methods and agents for inhibiting glycation.

More recently, other advanced glycosylation products have been identified, such as AFGP (Farmar et al., U.S. Pat. No. 5,017,696, issued May 21, 1991); pyrraline (Hayase et al., "Aging of Proteins: Immunological Detection of a Glucose-derived Pyrrole Formed during Maillard Reaction in vivo", *J. Biol. Chem.*, 264:3758–3764 (1989)), and pentosidine (Sell, D. and Monnier V. "Structure Elucidation of a Senescence Cross-link from Human Extracellular Matrix", *J. Biol. Chem.*, 264:21597–21602 (1989)).

A large body of evidence has been assembled to show that Maillard products as a whole underlie a wide variety of both normal and pathogenic activities and responses that occur as AGEs accumulate in vivo. Such activities may be direct, as a consequence of the chemical reactivity of glycation products and adducts; or indirect, mediated by the cellular recognition of glycation adducts and products via AGE-specific binding proteins or receptors.

Although most studies describing the pathogenic role of AGE accumulation in vivo have focused on AGE-proteins and AGE-peptides, the reaction between the lipids, and particularly, low-density lipoprotein (LDL) and glucose to form lipid-AGEs also has been determined to play a pathogenic role, for instance, in atherogenesis, where the formation of foam cells marks the accumulation of atherosclerotic plaques. Oxidation and glycation of the protein and lipid components of low-density lipoprotein (LDL) results in the loss of the recognition of the apo B component by cellular LDL receptors, prolonging the circulating half-life of this LDL and resulting in the preferential uptake of oxidized-LDL (ox-LDL) or otherwise modified LDL via macrophage "scavenger" receptors, AGE receptors, and other specialized cellular mechanisms. The enhanced endocytosis of ox-LDL by vascular wall macrophages has been linked to their transformation into lipid-laden foam cells that characterize early atherosclerotic lesions. Previous studies also have shown that AGE modification of LDLs increases the potential for lipid oxidation.

The "family" of AGEs includes relatively stable species which can be isolated and characterized by chemical structure, while others are unstable or reactive and their structural determination has therefore been problematic. Labile or reactive AGEs can be "trapped" by specific chemical agents, and such reactions and trapping have been used not only to gain structural insights but also to inhibit the glycation process for therapeutic purposes. AGE-lipids may also be stable unstable or reactive.

An appreciation for the pathogenic potential of AGEs has suggested that interference with, or inhibition of, advanced glycation chemistry could be of enormous therapeutic benefit. In this connection a series of agents has been discovered, as exemplified by aminoguanidine (also known as Pimagidine), that are useful glycation inhibitors. This compound, and others like it, have been theorized to react with the carbonyl moiety of the early glycosylation product of a target protein (or other biomolecule) formed subsequent to the initial nonenzymatic reaction with glucose or another reducing sugar, and thereby prevent further reaction to form advanced glycosylation endproducts.

A variety of other inhibitors of advanced glycation reactions are also known, many of which are thought to be particularly effective at stages of the Maillard reaction other than those which are most susceptible to inhibition by aminoguanidine and its analogs. For instance, certain compounds, or compositions thereof, having an active aldehyde substituent, such as acetaldehyde, are effective inhibitors of the advanced glycation pathway. This activity is thought to arise by the reaction of such active aldehyde agents with the glycosyl-amino moieties of glycation products formed in the initial stages of the Maillard reaction, i.e., these agents react with the Amadori and Heyns rearrangement products, which are early glycation products. Other agents, such as certain thiazolium compounds, are particularly effective at preventing advanced glycation, and even reversing the formation of advanced glycation endproducts and associated cross-linking moieties, through reactions with late glycation products.

The compounds, and their compositions, utilized in this invention are thought to react with early glycosylation products, thereby preventing the same from later forming the advanced glycosylation end products which lead to cross-links, and thereby, to molecular or protein aging and other adverse molecular consequences. All of such various glycation pathway inhibitors and other compounds reactive with early and late glycation products, either alone or in combination, find use in ameliorating the pathogenic potential of AGEs that accumulate in the body.

AGEs may accumulate through de novo formation in vivo, through reattachment of AGEs liberated in vivo by cellular activities, or as revealed herein by Applicants, by exposure to exogenous AGEs, for instance by smoking. Accordingly, the significance of the reactive pathways of AGEs and their observed presence in tobacco and tobacco smoke lends further importance and encouragement to the need for the development of effective techniques for monitoring the smoking habits of individuals. Such techniques would be useful for gathering the history of such smokers, and also for monitoring their medical condition and particularly, their predisposition to the conditions that are associated with elevated levels of AGEs. Measurement of AGEs in tobacco would facilitate the evaluation of tobacco crops, as well as providing an index of the amount of AGEs that would be transferred to a smoker during the consumption of smoking materials prepared from the crops in question; in this regard, AGEs may also be evaluated in tobacco smoke. It is toward the fulfillment of all of the above recited objectives that the present invention is directed.

SUMMARY OF THE INVENTION

The present invention derives from the discovery that tobacco and its combustion byproducts such as smoke, contain advanced glycosylation endproducts (AGEs) which are, as a group, reactive with proteins, and that consequently, individuals who smoke or otherwise use tobacco generally exhibit increases in AGE levels. The elevation in such levels has been linked to an increased incidence of the pathologies associated with both AGE presence and smoking, such as increased risk for coronary disease, atherosclerosis and other maladies likewise associated with both conditions.

Accordingly, the invention extends to the measurement of AGEs in tobacco smoking materials and the combustion byproducts of tobacco, in biological samples taken from smokers, to assess their medical history, as well as by tobacco itself, to identify AGE levels and to thereby facilitate an estimate of the likelihood of exposure of an individual to such AGEs during smoking, or to provide information on the condition of the tobacco or tobacco products including, for example, to evaluate the age, flavor and/or storage status (freshness) of a tobacco crop.

More particularly, the measurement and evaluation of smokers would serve both to apprise the healthcare professional and the patient of any pathological conditions that may either have a high likelihood of onset, or that, if present, bear close periodic monitoring and/or indicate the need for therapeutic intervention, and to assess the extent and consequent risk that the smoker assumes from the smoking habit. The latter consideration would attend the evaluation of the patient as participant in a program for the purpose of stopping smoking, as well as to assess the extent of the test subject's smoking history, for insurance or like investigative purposes to confirm the cessation of tobacco use (or lack thereof).

The measurement of AGEs may be made by treating a sample of tobacco to form an extract in which AGEs are suspected to be present, followed by the analysis of the extract for such purpose. In one embodiment, the sample may be treated by combustion to form smoke, and the smoke is then examined for the presence and amount of AGEs. Alternately, the extract may proceed from a chemical treatment of the tobacco alone. One may also examine the body fluids and tissues of the smoker to determine the level and extent of AGEs present as a result of smoking. The results would be compared to a standard developed from non-smoking individuals otherwise sharing the same medical profile as the patient under test.

The invention includes the preparation of agents to specifically recognize tobacco-relate AGEs, such as antibodies that are specifically directed against the AGEs found in tobacco and tobacco smoke to facilitate the detection of tobacco-related AGEs and the evaluation of the medical status of tobacco smokers. Such agents would be incorporated into test kits and the like for use in the performance of such evaluations.

In a related aspect, dosimeters may be prepared with a substrate or carrier retaining and bearing a glycation target molecule, such as an amine-bearing moiety, fixedly associated therewith, and capable of reacting with AGEs present in a sample, be it a sample of ambient air or a biological sample taken from a patient. The dosimeter may be used in conjunction with the diagnostic protocols and test kits set forth herein.

The invention further extends to methods for detecting and measuring the levels of advanced glycosylation endproducts in individuals who smoke tobacco, by gathering a biological sample from such individuals and thereafter examining the sample for the presence and amount of advanced glycosylation endproducts. The sample gathered may extend to serum, saliva, urine or feces, and the techniques for detection and measurement have been developed and utilized with respect to AGEs in the past.

The invention thus predicated on the relationship between the formation of advanced glycosylation endproducts and the preparation and consumption of tobacco, lays the groundwork for a variety of diagnostic and evaluative applications. The implementation of the principles of the present invention is facilitated by the body of research and knowledge that has resulted from the intimate investigation of the phenomenon of advanced glycosylation by the inventors herein.

Accordingly, it is a principal object of the present invention to provide a method for the measurement of the extent and level of formation of advanced glycosylation endproducts in tobacco and its byproducts, and in the individuals who consume such products.

It is a further object of the present invention to provide a method as aforesaid that is capable of application for diagnostic purposes, to monitor the medical history of tobacco smokers and other users and to thereby avert the development of the severe pathological complications that attend the accumulation of advanced glycosylation endproducts and smoking.

It is a still further object of the present invention to provide a method as aforesaid that extends to the evaluation of tobacco to determine its storage status and organoleptic potential.

It is a still further object of the present invention to provide diagnostic assays and related materials that effectively identify tobacco-related advanced glycosylation endproducts and their presence in particular tobacco products and likewise can identify similar accumulations in consumers thereof.

Other objects and advantages become apparent to those skilled in the art from a consideration of the ensuing detailed description which proceeds with reference to the following illustrative drawings.

DETAILED DESCRIPTION OF THE INVENTION

The present invention derives from the relationship that has been identified between the consumption of tobacco and the development of increased levels of advanced glycosylation endproducts in such individuals. Initial observations resulted from investigation of levels of advanced glycosylation endproducts in a particular test population and the discovery of a link or correlation and particularly, the conjunction of increased levels of ApoB-AGE and coronary heart disease in such population with the fact that the individuals exhibiting such increased levels and disease were regular consumers of tobacco products. The initial observation prompted the study of the tobacco products themselves, which yielded the discovery that such products including the combustion byproduct of smoke, contained high concentrations of advanced glycosylation endproducts. The result of these initial discoveries has prompted further investigations and has resulted in the development of the various aspects of the present invention related to measurement and tobacco-related AGEs.

More particularly, the invention extends in its initial aspect to the examination of subjects having a history of smoking to better determine their smoking history, by measuring the increases of advanced glycosylation endproducts over a norm derived from a non-smoking population having otherwise a similar or identical medical profile. Such methods may be practiced by the examination of a variety of body fluids of the test subject, including blood, urine and feces.

In similar fashion, the tobacco products themselves may be examined and evaluated to determine their potential for the promotion of increased AGE levels in tobacco users. In such instance, both the tobacco product itself and its combustion byproducts may be examined for the presence of such advanced glycosylation endproducts. In a related aspect, the same products may be examined and the level of advanced glycosylation endproducts indexed with a view to determining the storage stability and flavor potential of a given tobacco crop. Such measurements would be developed against certain benchmarks or standards taken from like samples or populations as the case may be.

In this connection, a variety of specific implementations of the protein-browning assay and an AGE-trapping filter that may be prepared in accordance with the present invention, also provides and exemplifies the essential elements required for a smoke-exposure dosimeter convenient for the estimation of the exposure of individuals to environmental smoke, especially tobacco smoke, based on the detection of AGEs that become cross-linked to protein amino groups or other susceptible chemical glycation targets. Applicants recognize that the dilution of tobacco smoke in the atmosphere can be estimated by dosimeter devices that are formulated to capitalize on the covalent reactions that occur between tobacco smoke-related AGEs and proteins or other molecules with free amino groups or other substituents that act as glycation target molecules, whereby said glycation target molecules are susceptible to chemical reaction with tobacco-related AGEs, causing said AGEs to become covalently cross-linked to said glycation target molecules and thereby detectable by means described herein.

The risk of exposure to environmental tobacco smoke can be estimated using a dosimeter of the present invention that exposes glycation target molecules to the atmosphere of an environment in need of monitoring for tobacco smoke burden, wherein said dosimeter provides for said reactive air-borne AGEs deriving from tobacco smoke to attach spontaneously to the AGE target molecules which are displayed on a matrix, thus comprising of the capture elements of the dosimeter. The AGEs that become attached to the amino group-displaying matrix of the dosimeter may be visualized, qualitatively, semi-quantitatively or quantitatively, by any of a number of AGE-identifying methods well-known in the art including, without limitation, the AGE ELISA method utilizing anti-AGE antibodies as described supra, in steps that comprise the display elements of the dosimeter. Suitable glycation target molecules for incorporation in the capture elements of the dosimeter include not only various proteins, such as BSA, collagen and poly-lysine that are well-known as AGE susceptible target molecules, but also any other biomolecules or organic compounds that present amino groups which are susceptible to reaction with AGEs.

Such glycation target molecules are preferably immobilized on the surface of a substrate which advantageously presents them to the atmosphere to be monitored; such as a paper surface derivatized to display amino groups, a nitrocellulose membrane surface similarly derivatized, a polystyrene filter surface likewise derivatized to present amino groups as glycation targets, or any other relatively inert matrix that presents glycation target molecules and is disposed to interact with the atmosphere of the environment to be monitored. Contact between the atmosphere to be monitored for tobacco smoke and the matrix-immobilized glycation target molecules, and circulation of said atmosphere over said capture elements, may be effected passively, as by convection, or actively, by any means that forces the atmosphere to flow over the capture elements, such as a fan. Alternatively, the amino-group presenting glycation target molecule may be dispersed in a liquid, and air from the environment to be monitored may be drawn through said liquid, for instance by bubbling. In either case, the glycation target molecules having been exposed to the atmosphere of the environment in need of monitoring, whether disposed on a matrix or within a fluid phase, are then examined by any suitable AGE-detecting method, such as specific implementation of the general AGE ELISA assay methods disclosed supra for the detection of AGEs, such that the detection of AGEs by their reaction with the glycation target molecules will indicate the degree of contamination of the environmental atmosphere with tobacco smoke. Use of such dosimeters will correspondingly indicate the exposure of individuals to secondhand smoke in the environment.

The dosimeters and corresponding methods of measurement recited above may be applied in a therapeutic context, to monitor and evaluate the course of treatment of a particular patient whose malady is characterized by elevated levels of AGEs in body fluids and tissues. Accordingly, a sample taken from the patient may be placed in contact with the dosimeter, and the extent of reaction of AGEs present in the sample may thereafter be measured by an AGE ELISA or like test, to apprise the treating physician of the patient's progress under treatment. The physician may then choose to modify the treatment regimen within discretion, based upon the results of the test. Equally relevantly, the measurement of both the sample taken from the patient and the ambient air in which the patient spends a preponderant amount of time, may suggest that the ambient should be remediated to reduce the exposure of the patient to additional sources of AGEs, whether from tobacco smoke or other exogenous sources, and consequently, will further aid the physician in caring for the patient.

Concomitant with the above, various diagnostic assays, kits and the like may be prepared which would be specifically useful in accordance with the present invention, by the preparation of antibodies that are directed to the advanced glycosylation endproducts found in tobacco and tobacco byproducts. Such antibodies may thereby be generated and thereby utilized as standards in diagnostic tests, as well as in the characterization of tobacco-related AGE structure.

The following examples are provided as illustrative of the experiments that have been performed to identify this relationship and to facilitate the implementation of the above inventive embodiments.

EXAMPLE 1

Figure 1:
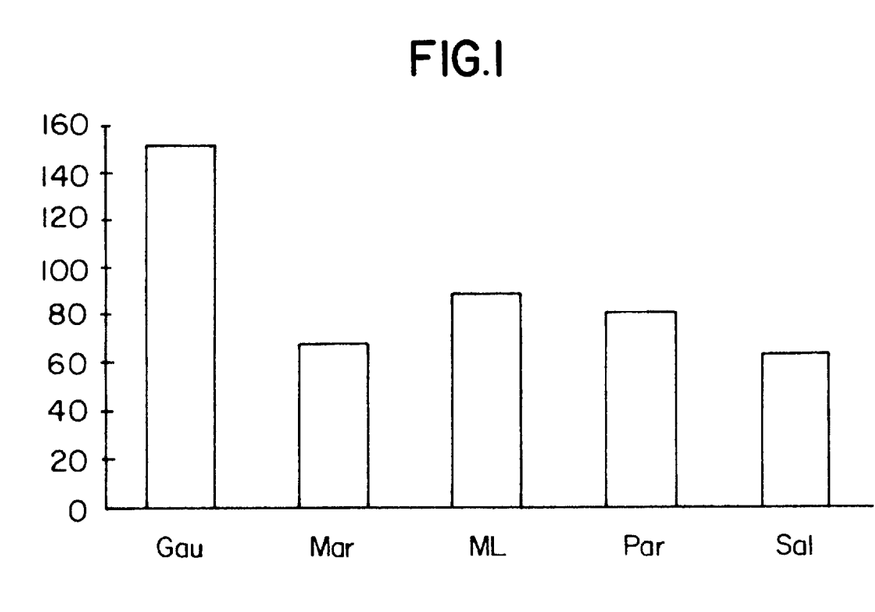
FIG. 1 is a graph showing the AGE content of aqueous extracts of cigarette tobacco. AGE levels in phosphate buffer extracts of cigarette tobacco samples were quantified in a standardized competitive AGE immunoassay and calculated as Total AGE Units per Cigarette. Cigarette brands were: Gau, Gauloises; Mar, Marlboro; ML, Marlboro Light; Par, Parliament; Sal, Salem Ultra Lights.

To determine whether AGEs are present in tobacco products, tobacco samples from several commercially available cigarette brands were prepared in 0.02M phosphate buffer, pH 7.4, at a tobacco concentration of 66.7 mg/ml. After an overnight incubation at room temperature, the tobacco was pelleted by centrifugation and the aqueous tobacco extract was filter sterilized, diluted 1:800, and analyzed for AGE content. Dilutions of the aqueous tobacco extracts were assayed for AGE content in a standardized competitive AGE immunoassay utilizing an anti-AGE monoclonal antibody (see below), which assay measures Units of AGE immunoreactivity relative to a reference standard competitor preparation of AGE-modified bovine serum albumin (AGE-BSA). From the assay results, Total AGE Units per Cigarette were calculated as an index of the AGE content of the extracts, and, as shown in FIG. 1, the extractable AGE content of these tobacco samples ranged from about 50,000 to 150,000 AGE Units per cigarette.

From this evidence. Applicants concluded that extremely high AGE-like immunoreactivity is present in aqueous extracts of tobacco. This suggested to Applicants that consumers of tobacco products including, for instance, snuff and chewing tobacco, or the smoke from combustible forms such as cigars, cigarettes or pipe tobacco, may be exposed to AGEs in large amounts through their tobacco consumption.

A competitive ELISA for AGEs is conducted according to general immunoassay procedures that are common in the art. Briefly, a Master Stock of AGE-modified BSA (AGE-BSA)

was prepared by incubating BSA (Calbiochem, Cat. #12657, Fraction V, purity >99% by SDS-PAGE) at 50 mg/ml in 0.5M glucose prepared in phosphate-buffered saline (PBS), pH 7.4, containing 1.0 mM EDTA and overlaid with a nitrogen atmosphere in sealed tubes for eight weeks at 37° C. Commercially available 96-well microtiter assay plates (NUNC Maxisorp) are coated with the standard antigen by incubating 100 μl of a solution of AGE-BSA at a concentration of 30 μg/ml in Coating Buffer (0.1M $NaHCO_3$/0.02% azide, pH 9.6) in each well overnight at 4° C. covered. Assay wells are then rinsed six times with 200 μl Wash Buffer (Tris-buffered saline with 0.05% Tween 20) using an automated ELISA plate washer, inverted, and blotted to dry. Each well then receives 200 μl Blocking Buffer (PBS/2% normal goat serum/0.2% BSA/0.02% azide, pH 7.4) and the plate is incubated, covered, for 1 hour at 37° C. After a rinsing as above, the standard AGE-BSA-modified assay plate is ready for use in the competitive ELISA.

The assay method of the present Example was initiated by addition of a 50 μl aliquot of sample or AGE-BSA Standard Competitor to each well of an AGE-BSA-coated assay plate, followed by the immediate addition 50 μl of an appropriately titrated preparation of an anti-AGE antibody. The plate was then incubated, covered, for two hours at room temperature, during which period AGEs within the test sample (or the AGE-BSA standard) competed for binding with the primary or anti-AGE antibody against the AGEs immobilized on the assay plate in the form of AGE-BSA. Ultimately, in this competitive immunoassay format, higher amounts of AGEs in the sample are reflected in higher competition against the coated AGE-BSA with corresponding diminishment of the final readout signal, the intensity of which reflects the degree of binding of the primary anti-AGE antibody to the AGE-BSA-coated well.

In this example, an anti-AGE monoclonal antibody, designated 4G9, was used at a dilution that provided approximately 1.5 optical density (OD) Units after the two hour final incubation with the chromogenic substrate in wells that received no competitor. A dilution series of AGE-BSA Standard Competitor was prepared by diluting AGE-BSA Master Stock to provide a concentration series ranging from about 0.1 to 2 μg AGE-BSA per well, and the equivalent concentration of AGE-BSA Standard Competitor corresponding to the final OD of each sample well could be interpolated from this standard competition curve. One AGE Unit is operationally defined as the concentration of Standard Competitor AGE-BSA (in BSA mg/ml) required for 50% inhibition in this competitive AGE ELISA format.

After this incubation of primary antibody and competitor (sample or standard), the wells were rinsed six times with Wash Buffer, inverted and blotted to dry. A commercially available preparation of secondary antibody-enzyme conjugate (for instance, anti-mouse IgG antibodies raised in goat, coupled to alkaline phosphatase) is then added and incubated according to the manufacturer's recommendations, typically as a 100 μl aliquot at a dilution of 1:1200 for 45 minutes at 37° C. Of course a variety of primary (anti-AGE) antibodies, either polyclonal or monoclonal or a mixture thereof, as well as a variety of means of detecting the binding of these primary antibodies, can be substituted in this procedure by relying on general immunoassay principles well understood in the art. In the present Example, the plates were then rinsed as above and a 100 μl aliquot of substrate chromogen (in this case, para-nitrophenyl phosphate (PNPP)) was added at a concentration recommended by the manufacturer and incubated, typically at 37° C. for 1–2 hours, to provide an OD of 1.5–1.7 Units in the control wells assayed in the absence of any competitor. Absorbance (OD) in each well may be read conveniently using a commercial microtiter plate reader, in this instance set to read at 410 nm versus a reference wavelength of 570 nm. The AGE level in any sample may then be interpolated as the equivalent concentration of Standard Competitor AGE-BSA (in BSA mg/ml) from the standard competition curve, and this value is then typically converted into AGE Units where 1 AGE Unit is the concentration of Standard Competitor AGE-BSA that produces 50% inhibition in this competitive AGE ELISA method.

EXAMPLE 2

To determine whether the AGEs present in tobacco smoke are reactive with the body's proteins, cigarette smoke was drawn through a 1 ml sample of normal human serum using a "hookah" or water-pipe smoking device constructed from a small class sidearm flask which was designed and operated not only to bubble a stream of smoke through the contained serum sample, but also to allowed smoke to accumulate above, and in contact with, the serum sample, which exposure was maintained during an incubation period following the active "smoking" phase of exposure. Filters were removed from the cigarettes to be used, and a cigarette was mounted in a Pasteur pipette that penetrated the stopper of the flask to terminate with its tip submerged in the serum sample. Once assembled, this device was repeatedly operated to draw the smoke from five (5) cigarettes through the serum sample by suction applied with a syringe attachable to the sidearm. Approximately the same volume of air was drawn through a separate serum sample using an identical device except that no cigarette supplied smoke to the airstream for this control reaction. AGE levels in these experimentally treated serum samples were then measured by the standardized competitive AGE ELISA described above (see Example 1).

Figure 2:
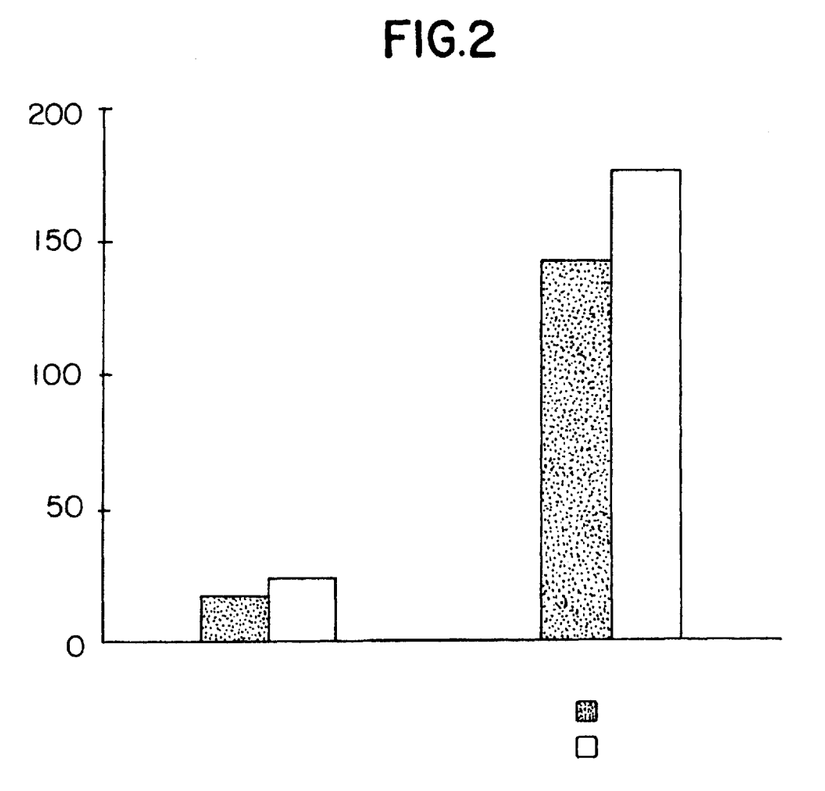
FIG. 2 is a graph showing AGE levels in serum experimentally exposed to tobacco smoke. AGE levels in serum samples through which cigarette smoke was bubbled were quantified in a standardized competitive AGE immunoassay and calculated as AGE Units per ml Serum. Control=a similar serum sample exposed only to an airstream, without tobacco smoke.

This experiment was conducted twice independently, with comparable results in each case as shown in FIG. 2. While control serum samples averaged less than 25 AGE Units per ml smoke-exposed serum samples showed about 150 AGE Units per ml. From this evidence, Applicants concluded that the AGEs present in tobacco smoke were reactive and were likely to attach to human proteins during smoking, increasing the AGE burden of smokers and providing a ready marker of the intensity of their recent smoking activity.

EXAMPLE 3

In a further test to determine whether AGE-like immunoreactive components are present in tobacco smoke, and to determine whether such AGEs are reactive with proteins, condensates of tobacco smoke were assessed for reactive AGE content as follows. A sidearm flask was equipped with a stopper to which was fitted a short piece of rubber tubing with an Pasteur pipette attached. A syringe fitted to the sidearm was operated repeatedly to draw smoke from a total of 3–5 cigarettes into the flask, which was immersed during this period of smoke condensate collection in an acetone/dry ice bath. Cigarette smoke condensed on the walls of the chilled flask, and this condensate material was solubilized and extracted into warm neutral aqueous solution by rinsing the interior of the flask with five mls of 0.02M phosphate buffer. This condensate extract was filter sterilized and diluted 1:5 with additional phosphate buffer.

The presence of reactive AGEs in these extracts was then assessed in a direct binding immunoassay that uses anti-AGE antibodies to detect the covalent attachment of reactive AGEs to an immobilized collagen layer. Briefly, commercially available 96-well micro titer plates with rat tail tendon collagen immobilized on the surface of the wells (Collaborative Research) were exposed to dilutions of the smoke condensate extracts described above and incubated overnight, covered, at room temperature. AGEs that become immobilized on the surface by interaction with the tail tendon collagen are then assayed in accordance with the immunometric procedures outlined above for the competitive AGE assay: smoke extract-treated collagen-coated plates were sequentially rinsed, exposed to the 4G9 monoclonal anti-AGE antibody, rinsed, exposed to a commercially available goat anti-mouse IgG/alkaline phosphatase conjugate, rinsed, and supplied with an appropriate chromogenic substrate (e.g. PNPP) to generate a signal measured by optical density at 410 nm which quantitatively reflects the amount of AGE-like immunoreactivity that had accumulated on the plate by exposure to the tobacco smoke condensate extract relative to controls not treated with smoke condensate extract.

Figure 3:
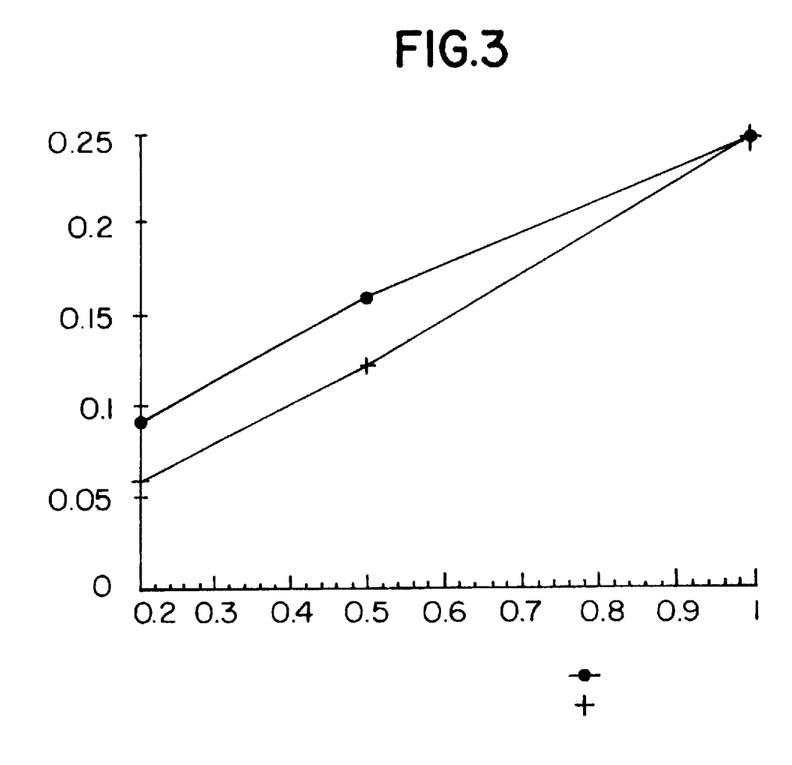
FIG. 3 is a graph showing that AGEs present in aqueous solutions of condensates of tobacco smoke are reactive with proteins in vitro. Collagen-coated assay plates were exposed to phosphate buffer-solubilized condensates of cigarette smoke, and AGEs present on the collagen-treated assay plate wells were measured by an immunometric method whereby an increase in the final absorbance (optical density or OD) reflects increased AGE crosslinking to, and accumulation on, the collagen matrix of the assay plate.
Figure 4:
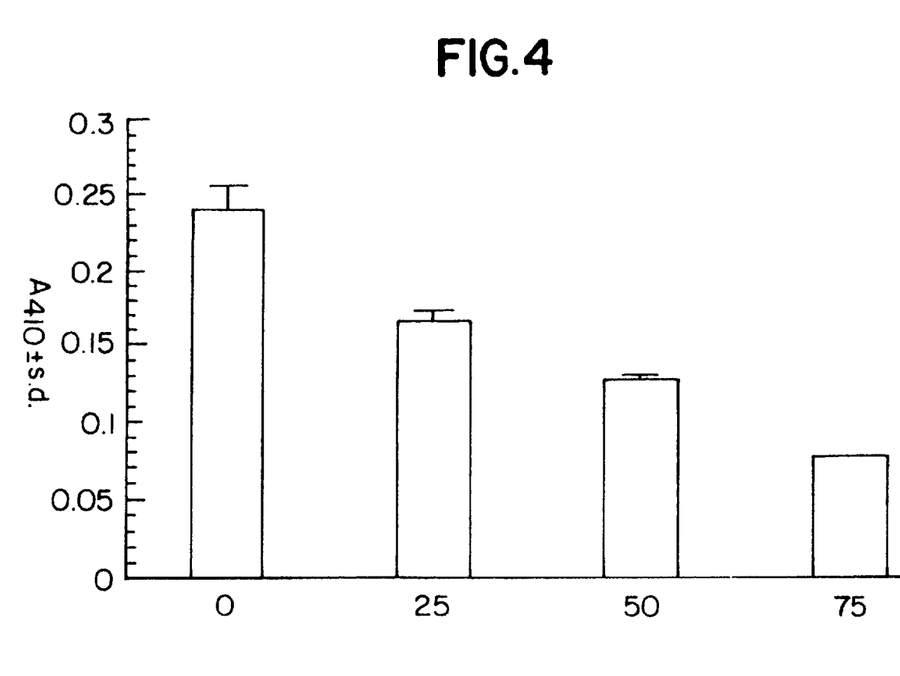
FIG. 4 is a graph showing that Pimagidine (aminoguanidine) inhibits the in vitro reaction of cigarette smoke condensate extract with protein. Collagen-coated assay plates were exposed to aqueous extracts of condensates of cigarette smoke in the presence of absence of various concentrations of Pimagidine. AGEs present on the collagen-treated assay plate wells were then measured by an immunometric method whereby an increase in the final absorbance (optical density or OD) reflects increased AGE crosslinking to, and accumulation on, the collagen matrix of the assay plate.

As shown in FIG. 3, there is more AGE-like immunoreactivity in wells exposed to tobacco smoke condensate extract, and the signal from these smoke-related AGEs decays with dilution of the extracts in close conformity with the dilution of glucose-derived AGEs formed in vitro as a standard for such comparisons. This indicated to Applicants that exposure to tobacco smoke will correspondingly expose the subject to AGEs that are reactive with natural proteins.

EXAMPLE 4

To determine whether an increase in AGE-like immunoreactivity could be measured after a defined exposure to tobacco smoke, blood samples were obtained from a subject who habitually smoked, first after an 18-hour hiatus in smoking behavior, and then after subject smoking five cigarettes consecutively at the end of the 18-hour hiatus. The degree of AGE modification of apoB was then compared in LDL fractions from these blood samples, using a standardized sandwich-type ELISA procedure to detect AGE-ApoB. In performing this standardized assay, an anti-AGE antibody is immobilized on the surface of the assay wells to capture AGE-modified components of the sample, and a commercially available anti-apoB monoclonal antibody/horseradish peroxidase (HRP) conjugate is used to detect any AGE-modified apoB so immobilized by specific binding interaction with the immobilized anti-AGE antibodies.

Briefly, a low-density lipoprotein (LDL)-enriched serum fraction was prepared by treating a 100 $\mu$l serum sample with 900 $\mu$l 6.66% polyethylene glycol, m.w. 8000, for 15 minutes, centrifuging (14,000 rpm, 10 minutes), and solubilizing the resulting pellet in 100 $\mu$l 0.5% SDS overnight. To construct assay plates, an anti-AGE antibody, in this case the monoclonal antibody 4G9, is immobilized onto the surface of a micro titer plate by incubation at a titrated dilution, after which non-specific binding is blocked by replacing the capture antibody solution with a 1% solution of BSA. LDL-enriched serum fractions (or appropriately titrated dilutions of LDL standard) are then incubated in triplicate in the assay plates in a final concentration of 0.05% SDS in buffer arid incubated for one hour, at which time the plates are rinsed and a titrated dilution of commercially available anti-ApoB monoclonal antibody/enzyme conjugate (in this case anti-ApoB/horseradish peroxidase (HRP) conjugate purchased from Biodesign International and used at 1:500 dilution) is added to detect any bound ApoB. After a one hour incubation the plates are washed and a suitable chromogenic HRP substrate, such as o-phenyline diamine (OPD) is added and, after an appropriate incubation period, OD is read at 450 nm versus a 570 nm reference wavelength. In general accordance with principles well known in the art, optimal concentrations of various reagents (e.g., the coating antibody and the detector antibody) and the optimal pH, detergent concentrations, buffer compositions, incubation periods, and other particular features are varied one against the other in order to maximize the sample signal and minimize interfering non-specific background "noise" in this sandwich-type immunometric assay for AGE-modification of apoB.

The pre-smoking AGE-ApoB value in this experiment was 218±1 and the post-smoking value was 241±3 ApoB-AGE Units per mg apoB (where one ApoB-AGE Unit is defined as the activity of 1 $\mu$g/ml of a commercially available LDL standard (e.g., from Cappel). Applicants considered this evidence that smoking can acutely elevate AGE modification of a specific blood component, apoB of LDL. This suggests that measurement of AGE levels on sample components can provide information about the recent smoking history of a subject. Moreover, since AGE modification of LDL has been linked to pathogenic mechanisms that adversely effect human health, this further suggested to Applicants that smokers might benefit from interventions to limit excess AGE exposure that occurs as a result of tobacco consumption.

EXAMPLE 5

To discover whether AGE levels in a readily sampled tissue or fluid compartment reflect smoking history, Applicants examined serum samples obtained from consecutive patients presenting for pre-surgical screening at the North Shore University Hospital, Manhasset, N.Y. Some of these patients, by chance, were smokers (Group 1), others were non-smokers (Group 2). In this survey, the patient populations were not stratified or otherwise controlled for intensity of smoking, sex, age, health, or other characteristics that might have accounted for some of the variability in serum AGE levels. Serum AGE levels were determined by a competitive AGE ELISA method using a monoclonal anti-AGE antibody to detect AGEs relative to a standardized preparation of AGE-BSA (as detailed above in Example 1). Mean serum AGE levels were 200±80 for Group I (N=23) versus 150±30 for Group 2 (N=15). Comparison of this data set by t-test for independent means revealed that this difference was significant at the 0.05 probability level.

EXAMPLE 6

The AGEs of tobacco and tobacco products including, for example, tobacco smoke, also find utility as antigens or haptens, to elicit antibodies specifically directed to tobacco-related AGE structures. Such antibodies, likewise of the present invention, are useful in turn to identify tobacco-related AGE structures. By constructing immunoassays employing anti-tobacco related AGE antibodies of the present invention, for instance, the degree to which proteins are modified by tobacco-related AGEs can be measured. As discussed above, and depending on the half-life of the protein so modified, immunochemical measurement of AGE epitopes on a protein sample, such as serum proteins, provides an index of recent tobacco consumption, e.g. by smoking. Likewise, immunochemical detection of AGE epitopes on circulating and/or tissue proteins can be used to monitor the course of treatment with agents of the present invention, which agents are directed toward inhibition of the excess accumulation of AGEs through tobacco use by reacting with AGEs in tobacco or tobacco smoke.

Various haptens, antigens, and conjugated immunogens corresponding to the tobacco-related AGEs of the present invention can conveniently be prepared, either by isolation of tobacco-related AGEs from tobacco or from tobacco smoke, for instance by making an AGE-containing aqueous extract of tobacco or of tobacco smoke condensate, as described above. This extract may then be used as an immunogen to raise a variety of antibodies which recognize specific epitopes or molecular features t hereof. In a preferred embodiment, the AGEs of the extract are considered haptens, which are correspondingly coupled to any of several preferred carrier proteins, including for instance keyhole limpet hemocyanin (KLH), thyroglobulin, and most preferred, bovine serum albumin (BSA), using any of a number of well-known divalent coupling reagents such as a carbodiimide like EDC, according to protocols widely circulated in the art. Irrespective of the source, the tobacco-related AGEs whether alone or coupled to a carrier protein, and whether pure or in partially purified form, may be employed in any well-recognized immunization protocol to generate antibodies and related immunological reagents that are useful in a number of applications owing to the specificity of the antibodies for molecular features of the tobacco-related product.

Following a preferred protocol, any of several animal species may be immunized to produce polyclonal antisera directed against the tobacco-related AGE protein conjugate, including for instance mice, rats, hamsters, goats, rabbits, and chickens. The first of three of the aforesaid animal species are particularly desired choices for the subsequent production of hybridomas secreting hapten-specific monoclonal antibodies. The production of said hybridomas from spleen cells of immunized animals may conveniently be accomplished by any of several protocols popularly practiced in the art, and which describe conditions suitable for immortalization of immunized spleen cells by fusion with an appropriate cell line e.g. a myeloma cell line. Said protocols for producing hybridomas also provide methods for selecting and cloning immune splenocyte/myeloma cell hybridomas and for identifying hybridomas clones that stably secrete antibodies directed against the desired epitope(s). Animal species such as rabbit and goat are more commonly employed for the generation of polyclonal antisera, but regardless of whether polyclonal antisera or monoclonal antibodies are desired ultimately, the hapten-modified carrier protein typically is initially administered in conjunction with an adjuvant such as Complete Freund's Adjuvant. Immunizations may be administered by any of several routes, typically intraperitoneal, intramuscular or intradermal; certain routes are preferred in the art according to the species to be immunized and the type of antibody ultimately to be produced. Subsequently, booster immunizations are generally administered in conjunction with an adjuvant such as alum or Incomplete Freund's Adjuvant. Booster immunizations are administered at intervals after the initial immunization, generally one month is a suitable interval, with blood samples taken between one and two weeks after each booster immunization. Alternatively, a variety of so-called hyperimmunization schedules, which generally feature booster immunizations spaced closer together in time, are sometimes employed in an effort to produce anti-hapten antibodies preferentially over anti-carrier protein antibodies.

The antibody titers in post-boost blood samples can be compared for hapten-specific immune titer in any of several convenient formats including, for instance, Ouchterlony diffusion gels and direct ELISA protocols. In a typical direct ELISA, a defined antigen is immobilized onto the assay well surface, typically in a 96-well or microtiter plate format, followed by a series of incubations separated by rinses of the assay well surface to remove unbound binding partners. By way of non-limiting example, the wells of an assay plate may receive a dilute, buffered aqueous solution of the hapten/carrier conjugate, preferably wherein the carrier protein differs from that used to immunize the antibody-producing animal to be tested; e.g. serum from tobacco-related AGE/KLH conjugate-immunized animal might be tested against assays wells decorated with immobilized tobacco-related AGE/BSA conjugate. Alternatively, the assay surface may be decorated by incubation with the hapten alone. Generally, the surface of the assay wells is then exposed to a solution of an irrelevant protein, such as casein, to block unoccupied sites on the plastic surfaces. After rinsing with a neutral buffered solution that typically contains salts and a detergent to minimize non-specific interactions, the well is then contacted with one of a serial dilution series of anti-serum prepared from the blood sample of interest (the primary antiserum). After rinsing again, the extent of test antibodies immobilized onto the assay wells by interaction with the desired hapten or hapten/carrier conjugate can be estimated by incubation with a commercially available enzyme-antibody conjugate, wherein the antibody portion of this secondary conjugate is directed against the species used to produce the primary antiserum; e.g. if the primary antiserum was raised in rabbits, a commercial preparation of anti-rabbit antibodies raised in goat and conjugated to one of several enzymes, such as horseradish peroxidase, can be used as the secondary antibody. Following procedures specified by the manufacturer, the amount of this secondary antibody can then be estimated quantitatively by the activity of the associated conjugate enzyme in a colorimetric assay. Many related ELISA or radioimmunometric protocols, such as competitive ELISAs or sandwich ELISAs, all of which are well known in the art, may optionally be substituted, to identify the desired antisera of high titer; that is, the particular antisera which give a true positive result at high dilution (e.g. greater than 1/1000 and more preferably greater than 1/10,000).

Similar immunometric protocols can be used to estimate the titer of antibodies in culture supernatants from hybridomas prepared from spleen cells of immunized animals. In so characterizing antisera or hybridoma supernatants, it is desirable to employ a variety of control incubations, e.g. with different carrier proteins, related but structurally distinct haptens or antigens, and omitting various reagents in the immunometric procedure in order to minimize non-specific signals in the assay and to minimize non-specific signals in the assay and to identify reliable determinations of antibody specificity and titer from false positive and false negative results. The types of control incubations to use in this regard are well known. Also, the same general immunometric protocols subsequently may be employed with the antisera identified by the above procedures (i.e., antibodies found to be of high titer and to be directed against specific structural determinants of tobacco-related AGEs). Such latter applications of the desired anti-tobacco-related AGE antibodies, whether polyclonal or monoclonal, together with instructions and optionally with other useful reagents and diluents, including, without limitation, a set of molecular standards of the tobacco-related AGES, may be provided in kit form for the convenience of the operator.

Anti tobacco-related-AGE antibodies generated as described, and particularly such monoclonal antibodies, also find use in the identification, separation, enrichment and purification of tobacco-related AGE epitopes. This may be accomplished by techniques known in the art, for instance, by exposing preparations known to contain the epitope of interest to immobilized antibodies specific for said epitope, washing away unbound material, and then eluting the specifically bound material and analyzing its chemical structure to determine specific molecular forms of tobacco-related AGEs.

EXAMPLE 7

To further demonstrate the utility of the AGE-inhibiting and AGE-reversing agents of the present invention to prevent the discoloration of protein on a surface, such as that which occurs on the tooth surface or on the skin or mucosal surfaces of smokers, the following surface browning experiment is performed. As a substitute for skin, mucosa or the pellicle-covered tooth surface, unexposed and developed photographic paper is used to provide an immobilized protein (gelatin, i.e., collagen) surface on a convenient paper backing. Five mm circles are punched from such photographic sheets, and several of these disks are then immersed in solutions of tobacco extract or tobacco smoke condensate (prepared as described above) that has been suitably diluted in an appropriate aqueous buffer (as described above), with or without an AGE-inhibiting or AGE-reversing agent of the present invention. Such experimental incubations are maintained, generally in the dark at a controlled temperature between 20° C. and 60° C., for a suitable time period which may range from several hours to several weeks. At various times after the incubation has been initiated, disks are recovered, observed for brown color and photographed for record keeping. Attachment of reactive AGEs from tobacco or smoke extracts causes the protein surface to become colored with yellow and brown AGE pigments, in a manner analogous to the staining of skin, a mucosal surface or the tooth pellicle of tobacco users. Prevention of the accumulation of AGEs, as evidenced by the prevention of accumulation of yellow/brown pigments with reference to control disks not incubated with the test agent, identifies AGE-inhibiting agents useful in the context of the present invention.

In an alternative assay for AGE-reversing activity, protein-covered disks are "pre-browned" by incubation with the diluted tobacco extract or tobacco smoke condensate extracts as described supra, and a candidate AGE-reversing agent of the present invention is added to the incubation solution for a further period of time. Inhibition or reversal of the accumulation of yellow/brown pigments by test agents of the present invention, by reference to control disks not incubated with the test agent, identifies candidates particularly suitable for use as AGE-reversing agents in the context of the present invention. AGE-inhibiting and AGE-reversing agents so identified are particularly suitable for formulation as an oral rinses or as a dentifrice to prevent or reverse undesirable tooth staining and pigmentation of other oral surfaces that occurs in conjunction with tobacco use, whether orally as with chewing tobacco and snuff, or by smoking as with cigarettes, cigars and pipe tobacco. Test agents with activity in this protein-browning assay may also be formulated into creams, emollients or the like for use on the stained hands and fingers of tobacco smokers.

EXAMPLE 8

Although cigarette smoking is widely accepted as a risk factor for cardiac, pulmonary, vascular, neoplastic and other diseases, the molecular mechanisms underlying this causal connection remain incompletely known. Both chronic and acute processes have been suggested to underlie pathogenic responses to tobacco use, but Applicants are the first to establish that tobacco consumption, particularly by smoking, can lead to elevated AGE levels in blood and tissues. Noting in their experiments that immunochemical staining with anti-AGE antibodies reveals that the coronary arteries of smokers with vascular diseases are heavily decorated with AGEs, Applicants also sought to confirm that chronic smoke exposure in vivo can lead to elevations in blood and tissue AGEs in a well-controlled animal model.

Using whole-body inhalation exposure chambers, six-week-old male and female rats (e.g., laboratory strain F344) are exposed, for various lengths of time ranging from a few weeks to 2 years, to an atmosphere of filtered air that is charged with a fixed burden of cigarette smoke particulates by dilution of mainstream smoke. Exposure for six hours per day, five days per week, for instance, to such an atmosphere carrying tobacco smoke at a level of 250 mg total particulate material (TPM) per cubic meter results in tobacco smoke deposits equivalent to those in the airways of humans smoking five packs of cigarettes per day. As described more fully in published procedures (e.g., J. Chen et al., 1989, *Inhalation Toxicol.* 1:331–347), mainstream smoke is generated from type IR3 non-filter research cigarettes (Tobacco Health Research Institute; Lexington, Ky.) using continuous smoking machines. Control animals are identically housed but exposed to the filtered airstream only, without cigarette smoke. Smoke exposure levels are determined by reference to gravimetric analysis of filter samples taken from the exposure chambers. The chemical and physical characteristics of this smoke-exposure atmosphere have been described in detail (vide supra and J. Chen et al., 1992, *J. Aerosol Med.* 5:19–30).

After the desired exposure period, test animals are sacrificed and various organs and tissues including, for instance, whole blood, are recovered and sampled for anatomical, microscopic, and biochemical analysis such as quantitation of AGE levels. In a preferred method, serum is diluted 1:5 in phosphate-buffered saline (PBS) and Proteinase K is added to 1/100 the mass of total serum protein in the sample. Serum proteins then are digested by incubation at 37° C., and Proteinase K is inactivated by raising the temperature to 70° C. for 1 hour. After a brief centrifugation to clarify, the supernatants are collected and brought to 1 mM phenymethylsulfonyl fluoride (PMSF) before analysis for AGE content by AGE ELISA as described supra.

In preliminary studies conducted according to this procedure, serum protein digests from rats exposed to cigarette smoke for periods ranging from 6–85 weeks showed pooled mean (±std. dev.) AGE levels of 22.0±4.9 AGE Units/ml serum (N=13), while control rats not exposed to cigarette smoke showed mean serum protein AGE levels of 13.5±2.9 AGE Units/ml serum (N=7). The above method also provides a convenient assay by which to estimate the activity of agents and filter devices of the present invention in inhibiting, preventing or reversing the accumulation of AGEs due to tobacco consumption, as either the tobacco itself, the primary or mainstream tobacco smoke, the smoke-laden atmosphere, or the smoke-exposed animals may be treated according to the present invention, and the tissues and blood of the test animals then examined to determine the degree to which AGE accumulation thereby has been diminished, prevented or reversed by comparison to untreated or unexposed control samples.

This invention may be embodied in other forms or carried out in other ways without departing from the spirit or essential characteristics thereof. The present disclosure is therefore to be considered as in all respects illustrative and not restrictive, the scope of the invention being indicated by the appended claims, and all changes which come within the meaning and range of equivalency are intended to be embraced therein.

What is claimed is:

1. A method for measuring the history of tobacco smoking, if any, in a human subject, comprising measuring the serum levels of advanced glycosylation endproducts (AGEs) or substances exhibiting immunoreactivity of AGEs in said subject, and comparing the results of said measurements to a pooled standard taken from non-smoking individuals of similar medical history.

2. A method for measuring the exposure of an individual to advanced glycosylation endproducts (AGEs) or substances exhibiting immunoreactivity of AGEs during tobacco smoking comprising measuring said AGEs or said substances in tobacco or in the volatilized combustion products thereof.

3. A method for determining the organoleptic potential of tobacco comprising measuring the presence and amount of advanced glycosylation endproducts (AGEs) or substances exhibiting immunoreactivity of AGEs in said tobacco.

4. A method for measuring the age and storage status of tobacco comprising measuring the presence and amount of advanced glycosylation endproducts (AGEs) or substances exhibiting immunoreactivity of AGEs in tobacco.

5. A method for determining the organoleptic potential of tobacco comprising measuring the presence and amount of advanced glycosylation endproducts (AGEs) or substances exhibiting immunoreactivity of AGEs in the smoke produced by the combustion of said tobacco.

6. A method for measuring the age and storage status of tobacco comprising measuring the presence and amount of advanced glycosylation endproducts (AGEs) or substances exhibiting immunoreactivity of AGEs in the smoke produced from the combustion of said tobacco.

7. A method for determining the commercial value of a particular tobacco crop comprising determining the organoleptic potential of tobacco and measuring its age and storage status by measuring the presence and amount of advanced glycosylation endproducts (AGEs) or substances exhibiting immunoreactivity of AGEs in a sample thereof.

8. The method of any of claims 2–6 or 7, wherein said AGEs or said substances are measured by:

A. Treating a sample of said tobacco to form an extract suspected of containing said AGEs or said substances; and B. Analyzing said extract to detect the presence and amount of any of said AGEs or said substances contained therein.

9. The method of claim 8, wherein said sample is treated by combustion to form smoke therefrom, and said smoke is examined for the presence and amount of said AGEs or said substances contained therein.

10. A method for detecting the presence and amount of advanced glycosylation endproducts (AGEs) or substances exhibiting immunoreactivity of AGEs in an individual who smokes tobacco, comprising:

A. gathering a biological sample from said individual, said biological sample selected from the group consisting of serum, saliva, urine and feces; and B. analyzing said sample for the presence and amount of said AGEs or said substances.

11. A method for the generation of antibodies enriched for reactivity with advanced glycosylation endproducts or moieties exhibiting immunoreactivity of AGEs present in tobacco and its combustion byproducts including tobacco smoke, comprising immunizing an animal with an immunogen selected from tobacco; tobacco smoke; the extracts thereof; carrier proteins derivatized with any of the foregoing; and haptens of said immunogen, optionally using a bi-functional crosslinking bridge reaction.

* * * * *